United States Patent
Hotomi et al.

(10) Patent No.: US 11,608,668 B2
(45) Date of Patent: *Mar. 21, 2023

(54) DAMPER AND DAMPER MONITORING METHOD

(71) Applicant: SIMOTEC CO., LTD., Higashiosaka (JP)

(72) Inventors: Hideo Hotomi, Higashiosaka (JP); Takashi Shimonishi, Higashiosaka (JP)

(73) Assignee: SIMOTEC CO., LTD., Osaka (JP)

( * ) Notice: Subject to any disclaimer, the term of this patent is extended or adjusted under 35 U.S.C. 154(b) by 429 days.

This patent is subject to a terminal disclaimer.

(21) Appl. No.: 16/650,420

(22) PCT Filed: Sep. 20, 2018

(86) PCT No.: PCT/JP2018/034914
§ 371 (c)(1),
(2) Date: Mar. 25, 2020

(87) PCT Pub. No.: WO2019/059311
PCT Pub. Date: Mar. 28, 2019

(65) Prior Publication Data
US 2020/0270925 A1    Aug. 27, 2020

(30) Foreign Application Priority Data

Sep. 25, 2017    (JP) .............................. JP2017-184238

(51) Int. Cl.
*E05F 3/14*    (2006.01)
*E05D 3/02*    (2006.01)
(Continued)

(52) U.S. Cl.
CPC .................. *E05F 3/14* (2013.01); *E05D 3/02* (2013.01); *F16F 9/12* (2013.01); *G01H 17/00* (2013.01);
(Continued)

(58) Field of Classification Search
CPC ....... E05F 3/14; E05D 3/02; F16F 9/12; F16F 2222/12; F16F 2232/02; G01H 17/00;
(Continued)

(56) References Cited

U.S. PATENT DOCUMENTS

| 4,674,606 A | 6/1987 | Denton |
| 4,674,608 A | 6/1987 | Morris et al. |

(Continued)

FOREIGN PATENT DOCUMENTS

| CN | 1880793 A | 12/2006 |
| CN | 102052260 A | 5/2011 |

(Continued)

OTHER PUBLICATIONS

CNIPA The Second Office Action for corresponding CN Application No. 201880062483.4; dated Sep. 9, 2021.

(Continued)

*Primary Examiner* — Nathaniel T Woodward
(74) *Attorney, Agent, or Firm* — Cantor Colburn LLP

(57) ABSTRACT

A damper is provided which can more reliably prevent malfunction and breakdown and which enables efficiently performing repair and inspection operations. This damper, provided with a casing linked to a first object and a rotating part linked to a second object rotatably attached to the first object, damps rotation in either the direction closing or the direction opening the second object, and is provided with a sensor which detects prescribed change in the external environment in the damper or around the damper, and a control unit which externally communicates, over a communication network, information relating to the change in the external environment detected by the sensor, wherein the sensor is configured from at least one of: a rotation sensor for detecting the number of revolutions of the rotating part: a sound sensor for detecting sound during rotations of the (Continued)

rotating part; a temperature sensor for detecting temperature; and a torque sensor for detecting torque on the basis of friction during rotation of the rotating part.

2 Claims, 7 Drawing Sheets

(51) Int. Cl.
| | |
|---|---|
| *F16F 9/12* | (2006.01) |
| *G01H 17/00* | (2006.01) |
| *G01J 1/00* | (2006.01) |
| *G01K 13/00* | (2021.01) |
| *G01L 3/00* | (2006.01) |
| *G01L 5/00* | (2006.01) |
| *G01N 33/00* | (2006.01) |
| *G01P 3/44* | (2006.01) |
| *G08C 15/00* | (2006.01) |

(52) U.S. Cl.
CPC ............... *G01J 1/00* (2013.01); *G01K 13/00* (2013.01); *G01L 3/00* (2013.01); *G01L 5/00* (2013.01); *G01N 33/0036* (2013.01); *G01P 3/44* (2013.01); *G08C 15/00* (2013.01); *E05Y 2201/256* (2013.01); *E05Y 2201/266* (2013.01); *E05Y 2800/17* (2013.01); *E05Y 2900/60* (2013.01); *F16F 2222/12* (2013.01); *F16F 2232/02* (2013.01)

(58) Field of Classification Search
CPC ... G01J 1/00; G01K 13/00; G01L 3/00; G01L 5/00; G01N 33/0036; G01P 3/44; G08C 15/00; G08C 17/00; E05Y 2201/256; E05Y 2201/266; E05Y 2800/17; E05Y 2900/60; E05Y 2400/20; E05Y 2400/44; E05Y 2400/458
USPC .......................................................... 73/23.2
See application file for complete search history.

(56) References Cited

U.S. PATENT DOCUMENTS

| | | | |
|---|---|---|---|
| 5,573,008 A | | 11/1996 | Robinson et al. |
| 5,573,088 A | * | 11/1996 | Daniels ................. F16F 9/10 |
| | | | 188/267 |
| 5,654,833 A | * | 8/1997 | Fujike .................... G02B 7/10 |
| | | | 396/137 |
| 7,756,619 B2 | | 7/2010 | Ichikawa et al. |
| 8,118,536 B2 | | 2/2012 | Krauss |
| 8,985,502 B2 | * | 3/2015 | Krysinski ............. B64C 27/001 |
| | | | 244/17.11 |
| 2002/0157909 A1 | | 10/2002 | Hasegawa et al. |
| 2006/0287788 A1 | | 12/2006 | Ichikawa et al. |
| 2010/0135793 A1 | | 6/2010 | Krauss |
| 2010/0211253 A1 | | 8/2010 | Morais Dos Santos et al. |
| 2015/0159730 A1 | | 6/2015 | Willems |
| 2018/0073590 A1 | | 3/2018 | Battlogg |
| 2019/0017724 A1 | | 1/2019 | Sekar et al. |

FOREIGN PATENT DOCUMENTS

| | | |
|---|---|---|
| CN | 10401900 A | 9/2014 |
| CN | 104019000 A | 9/2014 |
| JP | H0425631 A | 1/1992 |
| JP | H0544763 A | 2/1993 |
| JP | H112278 A | 1/1999 |
| JP | 2000018304 A | 1/2000 |
| JP | 2004271198 A | 9/2004 |
| JP | 2008304044 A | 12/2008 |
| JP | 2011500402 A | 1/2011 |
| JP | 2017160017 A | 9/2017 |

OTHER PUBLICATIONS

CNIPA The Second Office Action for corresponding CN Application No. 201880062308.5; dated Sep. 9, 2021.
CNIPA Office Action for corresponding CN application No. 201880062308.5; dated, Jan. 28, 2021.
CNIPA Office Action for Corresponding CN Application No. 201880062483.4; dated Jan. 28, 2021.
International Preliminary Report on Patentability for International Application No. PCT/2018/034812; dated Oct. 23, 2019.
International Preliminary Report on Patentability for international Application No. PCT/JP2018/034914; dated Sep. 10, 2019.
USPTO Non-Final Office Action for corresponding U.S. Appl. No. 16/650,414; dated May 26, 2021.
International Search Report; International Application No. PCT/JP2018/034812; International Application Filing Date Sep. 20, 2018; dated Dec. 18, 2018; 4 pages.
International Search Report; International Application No. PCT/JP2018/034914; International Filing Date Sep. 20, 2018; dated Dec. 18, 2018; 4 pages.

* cited by examiner

DAMPER AND DAMPER MONITORING METHOD

CROSS REFERENCE TO RELATED APPLICATIONS

This is the U.S. national stage of application No. PCT/JP2018/034914, filed on Sep. 20, 2018. Priority under 35 U.S.C. § 119(a) and 35 U.S.C. § 365(b) is claimed from Japanese Application No. 2017-184238, filed Sep. 25, 2017, the disclosure of which is also incorporated herein by reference.

TECHNICAL FIELD

The present invention relates to a damper that damps rotation of a second object rotatably attached to a first object in either a closing direction or an opening direction, and a damper monitoring method.

BACKGROUND ART

There has been known a technique concerning a damper that includes a casing linked to a first object, and a rotational part linked to a second object rotatably attached to the first object, the damper damping the rotation of the second object in either a closing direction or an opening direction (c.f. Patent Literature 1).

Specific examples of the use in which the damper is provided include: a use for damping the rotation in the closing direction of an original pressing plate rotatably attached to the body of a multi-function machine which includes an original reader; a use for damping the rotation in the closing direction of a hatch (lid) configured to exchange a toner cartridge rotatably attached to the body of a printer; a use for damping the rotation in the closing direction of a screen part rotatably attached to the body of a laptop computer or a mobile phone; a use for openably linking a hood rotatably attached to the body of a car; a use for damping the rotation in the closing direction of a toilet seat rotatably attached to a toilet; a use for damping the rotation in the closing direction of a lid rotatably attached to a pot of a rice cooker; and a use for damping the rotation in the closing direction of a window or a door rotatably attached to an opening that communicates with the inside of a furnace or a workroom.

As for the above damper, an external person such as a maintenance contractor has grasped the state of the damper such as a defect or a failure or the surrounding conditions of the damper mainly through periodically conducted inspection work, notification made by a user, or the like.

CITATIONS LIST

Patent Literature

Patent Literature 1: JP-A 11-2278 Gazette

SUMMARY OF INVENTION

Technical Problems

However, as for the above damper, the state of the damper or the surrounding conditions of the damper greatly vary depending on the installed environment, the use state, or the like. In addition, there are variations in inspection technique and attention among inspectors, users, and the like who are to grasp the state of the damper or the surrounding conditions of the damper.

There has thus been a case where, at the time of conduction of the periodic inspection work or reception of the notification from the user, it is already too late or a large-scale repair is required. There has also been a case where, by conduction of the periodic inspection work, reception of the notification from the user, or the like, the inspection work, the repair work, or the like is conducted even when the repair work or the like is not required.

The present invention has been made in view of the circumstances as described above, and it is an object of the present invention to provide a damper and a damper monitoring method, which can more reliably prevent a defect, a failure, and the like from occurring and efficiently conduct repair and inspection work.

Solutions to Problems

The problem to be solved by the present invention is as described above, and solutions to the problem will be described below.

That is, the solution is a damper including: a casing linked to a first object; and a rotational part linked to a second object rotatably attached to the first object, the damper damping rotation of the second object in either a closing direction or an opening direction, the damper including: a sensor that detects a predetermined change in an external environment in the damper or around the damper; and a control unit that transmits information on the change in the external environment, detected by the sensor, to the outside through a communication network, in which the sensor is constituted by at least any one of a rotation count sensor that detects the number of times of rotation of the rotational part with respect to the casing, a sound sensor that detects a sound of the rotational part during a rotating operation with respect to the casing, a temperature sensor that detects a temperature, and a torque sensor that detects torque based on a frictional force of the rotational part during rotation with respect to the casing, the control unit determines whether or not the external environment change detected by the sensor is higher than the predetermined threshold, when the external environment change detected by the sensor is higher than the predetermined threshold, the control unit transmits the information on the change in the external environment detected by the sensor to the outside, the predetermined threshold can be set in a plurality of stage, and the control unit can also be set to determine whether or not the external environment change detected by the sensor is higher than the predetermined threshold in each of the plurality of stage.

The solution is a monitoring method for a damper that includes a casing linked to a first object; and a rotational part linked to a second object rotatably attached to the first object, the damper being rotatably linking the second object to the first object, a sensor provided in the damper detecting a predetermined change in an external environment in the damper or around the damper; and a control unit transmitting information on the change in the external environment, detected by the sensor, to the outside through a communication network, in which the sensor is constituted by at least any one of a rotation count sensor that detects the number of times of rotation of the rotational part with respect to the casing, a sound sensor that detects a sound of the rotational part during a rotating operation with respect to the casing, a temperature sensor that detects a temperature, and a torque sensor that detects torque based on a frictional force of the rotational part during rotation with respect to the casing, the control unit determines whether or not the external environment change detected by the sensor is higher than the predetermined threshold, when the external environment change detected by the sensor is higher than the predetermined threshold, the control unit transmits the information on the change in the external environment detected by the sensor to the outside, the predetermined threshold can be set in a plurality of stage, and the control unit can also be set to determine whether or not the external environment change is higher than the predetermined threshold in each of the plurality of stage.

As the effects of the present invention, the following effects can be obtained.

That is, according to the present invention, it is possible to more reliably prevent a defect, a failure, and the like from occurring, and it is possible to efficiently conduct repair and inspection work.

DESCRIPTION OF EMBODIMENT

Next, a damper according to an embodiment of the present invention will be described with reference to FIGS. 1 to 7.

The damper damps the rotation of a second object rotatably attached to a first object in either a closing direction or an opening direction.

Specific examples of the use in which the damper is provided include: a use for damping the rotation in the closing direction of an original pressing plate rotatably attached to the body of a multi-function machine which includes an original reader; a use for damping the rotation in the closing direction of a hatch (lid) configured to exchange a toner cartridge rotatably attached to the body of a printer; a use for damping the rotation in the closing direction of a screen part rotatably attached to the body of a laptop computer or a mobile phone; a use for openably linking a hood rotatably attached to the body of a car; a use for damping the rotation in the closing direction of a toilet seat rotatably attached to a toilet; a use for damping the rotation in the closing direction of a lid rotatably attached to a pot of a rice cooker; and a use for damping the rotation in the closing direction of a window or a door rotatably attached to an opening that communicates with the inside of a furnace or a workroom.

Next, the box member 2 will be described as an example in which the damper is provided.

Figure 1:
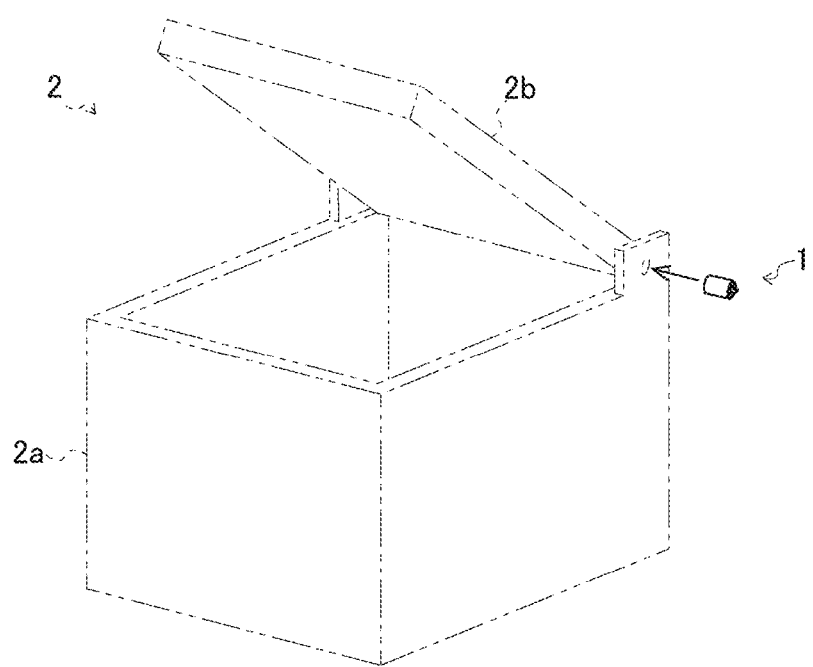
FIG. 1 is a right side view showing a box member provided with a damper according to an embodiment of the present invention.
Figure 2:
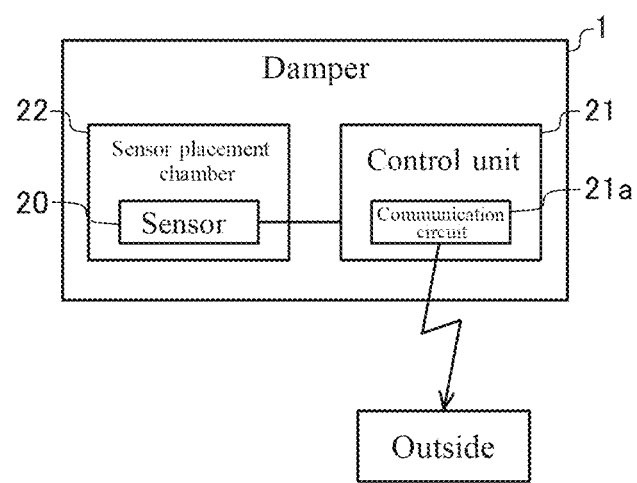
FIG. 2 is a block diagram showing the damper.

As shown in FIG. 1, the box member 2 includes a body 2a and a lid 2b, and the lid 2b is rotatably linked to the body 2a via the damper.

The body 2a is an embodiment of the first object to which the damper is linked. The body 2a has an opening in a part (upper part) thereof, and is configured so that a predetermined thing can be housed therein or predetermined work can be conducted inside.

The lid 2b is an embodiment of the second object to which the damper is linked. The lid 2b is disposed above the body 2a, and opens and closes the opening of the body 2a by rotating relatively to the body 2a.

Note that the one in which the damper is provided is not limited to such a configuration but broadly includes ones in which one member is rotatably linked to the other member via the damper.

Next, a damper 1 will be described as an example of the damper.

As shown in FIGS. 1 to 7, the damper 1 is a rotary damper and damps the rotation of the lid 2b, rotatably attached to the body 2a of the box member 2, in the closing direction.

The damper 1 includes a casing 1A made up of a tubular member 10 and a lid member 11, and a rotational part 1B made up of a shaft member 12, a clutch member 13, and a rotor 14. The clutch member 13 and the rotor 14 are housed inside the casing 1A. The casing 1A is linked to the body 2a of the box member 2, and the rotational part 1B is linked to the lid 2b of the box member 2.

The tubular member 10 is formed in a bottomed cylindrical shape and is sealed by the lid member 11 having an opening 11a at an opening opposite to the bottom, to constitute the cylindrical casing 1A. The body 2a of the box member 2 is fixed to the bottom of the tubular member 10 (casing 1A).

Figure 3:
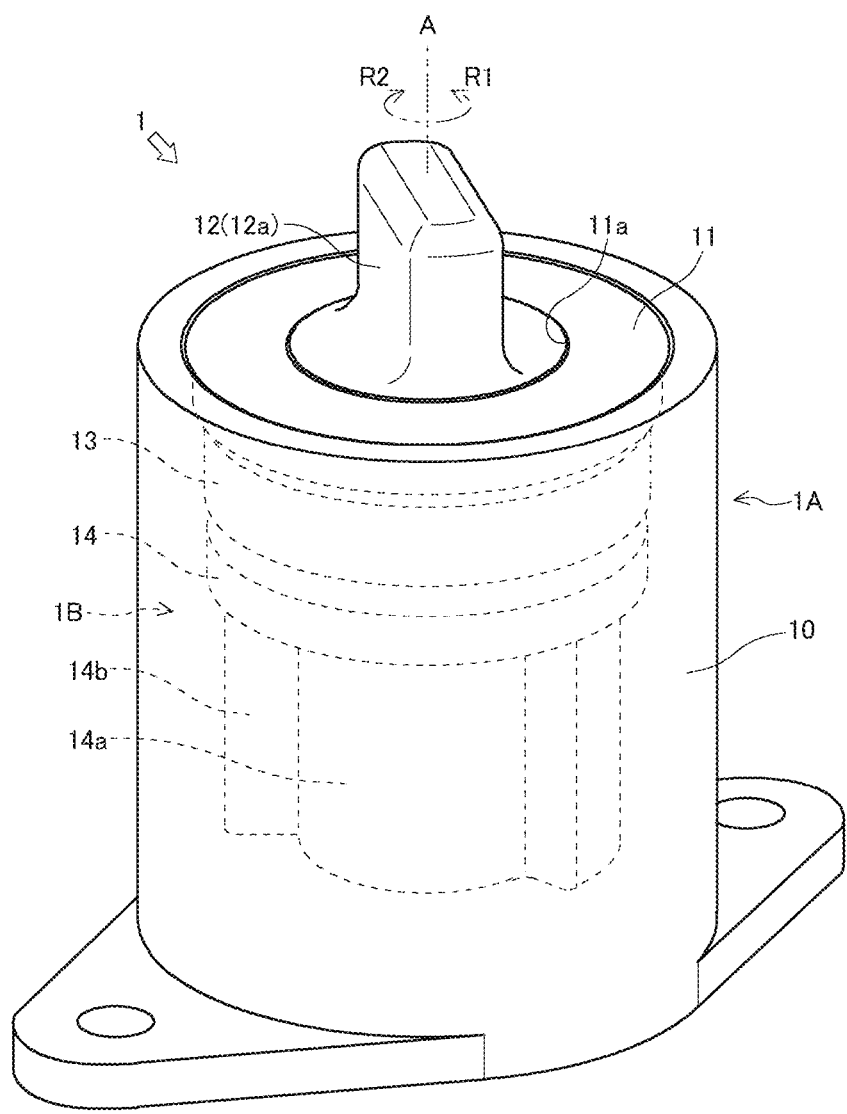
FIG. 3 is a perspective view showing the damper.
Figure 4:
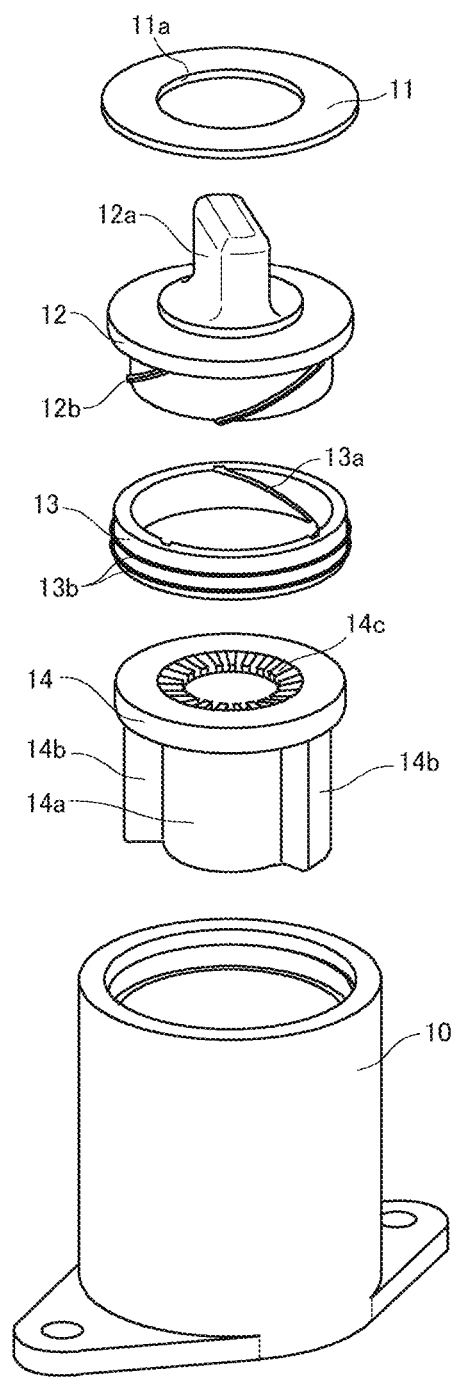
FIG. 4 is a perspective view showing a state where the damper has been disassembled.
Figure 5:
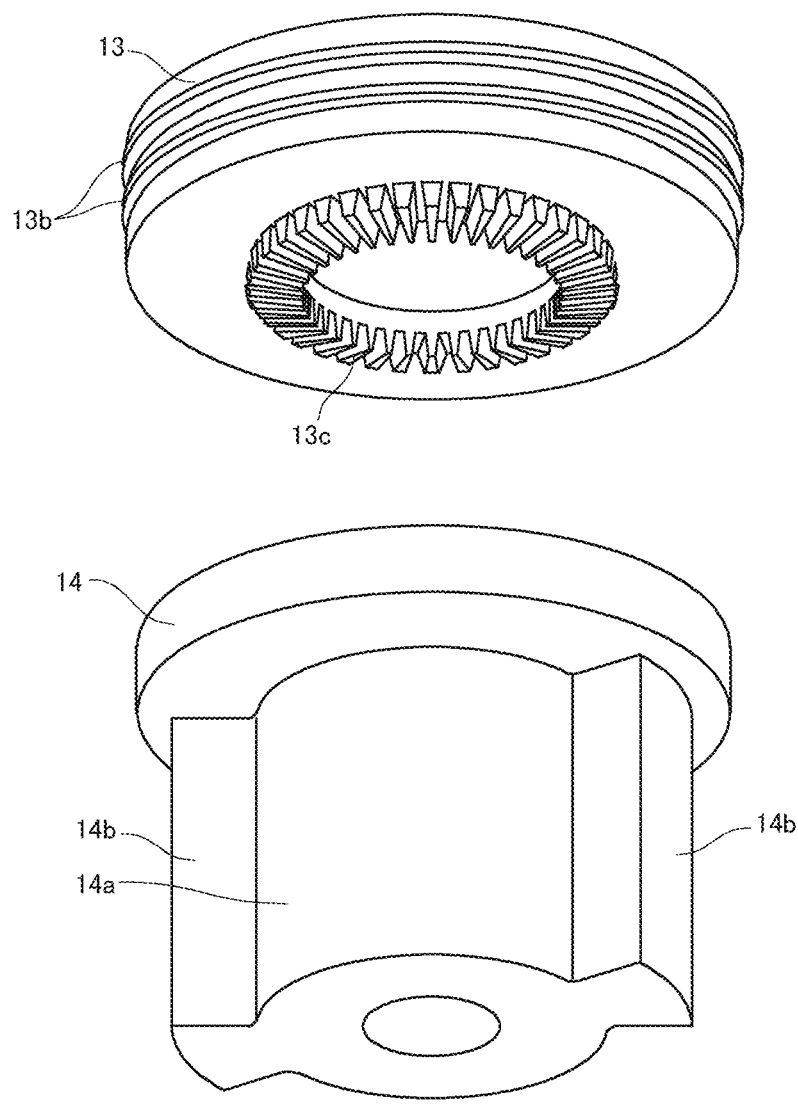
FIG. 5 is a perspective view showing a clutch member and a rotor of the damper.
Figure 6:
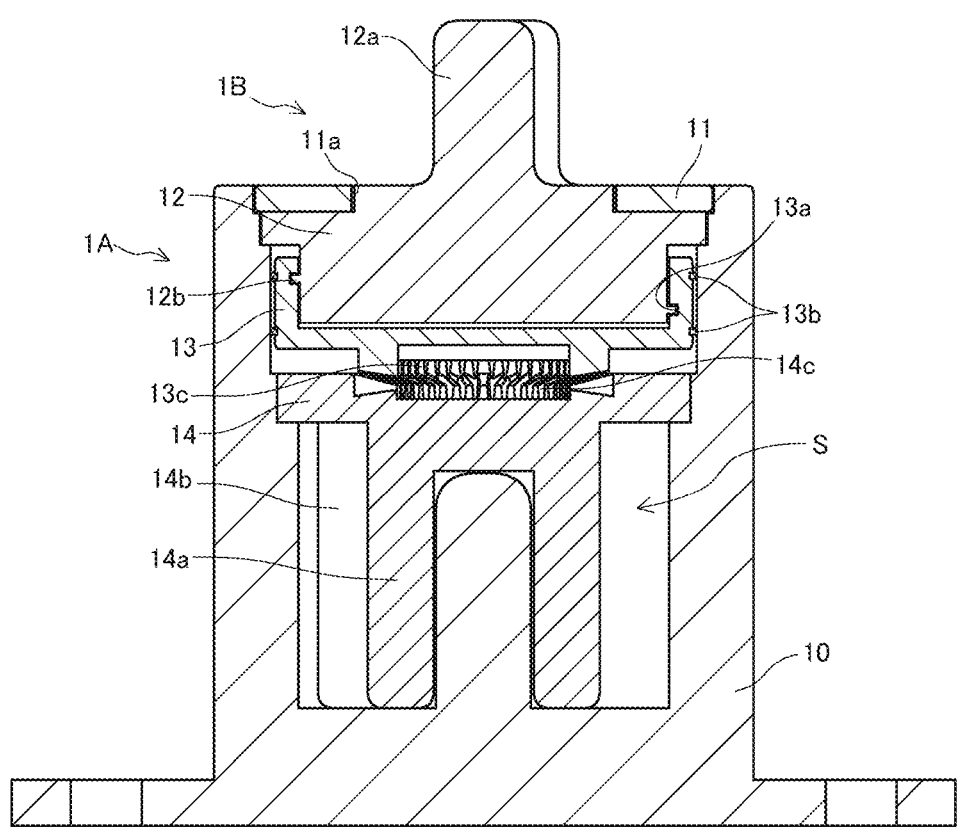
FIG. 6 is a sectional view showing the damper.
Figure 7:
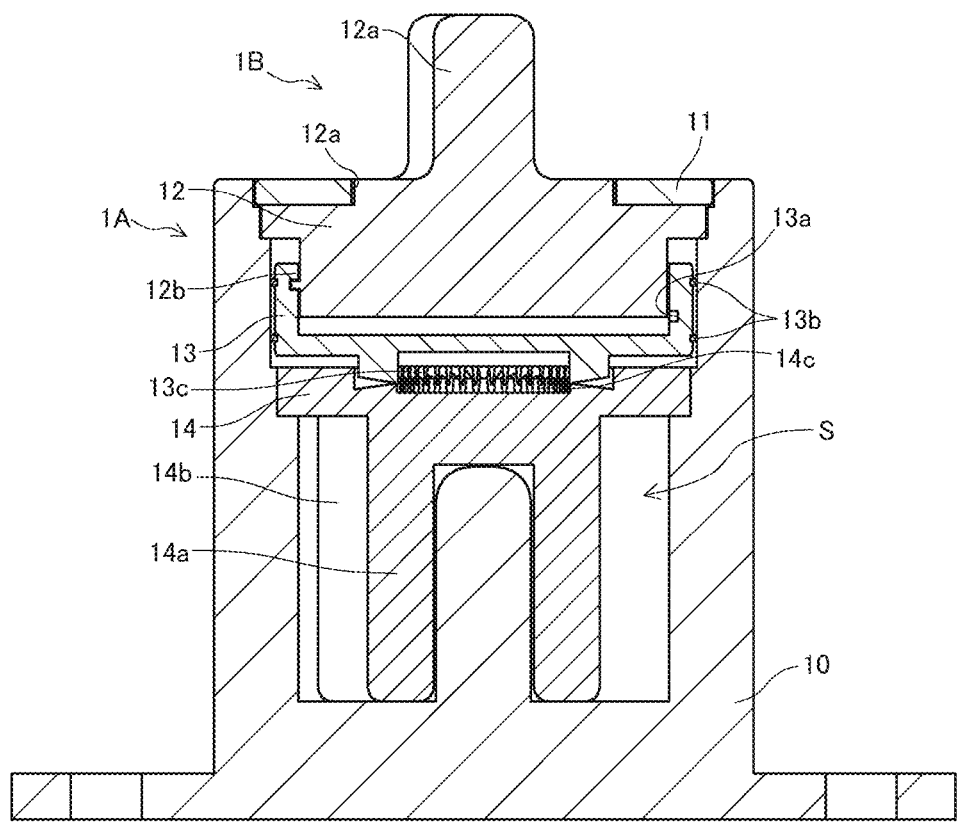
FIG. 7 is a sectional view showing the damper.

The shaft member 12 is housed in the upper inside of the casing 1A and is configured to be rotatable around an axis A of the casing 1A (cf. FIG. 3). An input part 12a is formed at the upper end that is one end of the shaft member 12, and the input part 12a extends from the opening 11a of the casing 1A. On the outer peripheral surface at the lower end of the shaft member 12, a male screw 12b is formed. The lid 2b of the box member 2 is fixed to the input part 12a (rotational part 1B).

The clutch member 13 is a bottomed cylindrical member that is housed in the casing 1A below and adjacent to the shaft member 12 and has an open-top. The clutch member 13 is disposed so as to be displaceable in the axial direction of the casing 1A (the vertical direction in FIG. 3). A female screw 13a is formed on the inner peripheral surface of the clutch member 13. The lower end of the shaft member 12 is inserted inside the clutch member 13, and the male screw 12b is screwed into the female screw 13a.

Further, O-rings 13b, 13b in contact with the inner peripheral surface of the tubular member 10 are provided on the outer peripheral surface of the clutch member 13. Thereby, sliding resistance is generated between the clutch member 13 and the inner peripheral surface of the tubular member 10, and the viscous fluid filling the lower side of the clutch member 13 is prevented from leaking upward. A clutch-side gear 13c is formed protruding from a surface (lower surface) of the clutch member 13 opposite to the shaft member 12.

The rotor 14 is a member that is housed below the inside of the casing 1A below and adjacent to the clutch member 13. The rotor 14 has an upper side formed in a substantially disc shape, and below the upper side, a cylindrical body 14a is disposed on the radial inside of the casing 1A. The rotor 14 is rotatable around the axis A of the casing 1A inside the casing 1A.

A rotor-side gear 14c that meshes with the clutch-side gear 13c is formed on the surface (upper surface) of the rotor 14 on the clutch member 13 side. That is, a gear (clutch-side gear 13c and rotor-side gear 14c) that meshes with each other is formed on the surface where the clutch member 13 and the rotor 14 face each other.

By filling a space (space S) between the body 14a of the rotor 14 and the inner peripheral surface of the tubular member 10 with a viscous fluid, the rotor 14 (specifically, a resistance part 14b of the rotor 14) is configured to generate rotational resistance when the rotor 14 rotates.

In the damper 1 configured as thus described, the clutch member 13 is displaced in the axial direction (vertical direction) as the shaft member 12 rotates. As the clutch member 13 moves downward, the clutch-side gear 13c and the rotor-side gear 14c mesh with each other. On the other hand, as the clutch member 13 moves upward, the clutch-side gear 13c and the rotor-side gear 14c are separated from each other.

When the clutch member 13 and the rotor 14 are separated from each other, the clutch-side gear 13c and the rotor-side gear 14c do not mesh with each other. When the shaft member 12 is rotated from this state in the direction of arrow R2 in FIG. 3 (clockwise), the clutch member 13 is displaced upward until coming into contact with the shaft member 12. At this time, since the clutch member 13 and the rotor 14 are kept separated, the rotational resistance of the rotor 14 is not transmitted to the shaft member 12. That is, the shaft member 12 receives only the sliding resistance of the clutch member 13 as the rotational resistance.

When the shaft member 12 is rotated in the direction of arrow R1 (counterclockwise) in FIG. 3 from the state where the clutch member 13 and the rotor 14 are separated from each other, the clutch member 13 is displaced downward, and the clutch-side gear 13c and the rotor-side gear 14c mesh with each other. At this time, since the clutch member 13 and the rotor 14 are linked, the rotational resistance of the rotor 14 is transmitted to the shaft member 12 via the clutch member 13. That is, since the shaft member 12 receives the rotational resistance of the rotor 14 in addition to the sliding resistance of the clutch member 13, a large rotational resistance is generated (rotational resistance increases) in the shaft member 12.

When the clutch member 13 and the rotor 14 are in the linked state, the clutch-side gear 13c and the rotor-side gear 14c mesh with each other. When the shaft member 12 is rotated from this state in the direction of arrow R1 in FIG. 3 (counterclockwise), the clutch member 13 remains linked to the rotor 14, so that the rotational resistance of the rotor 14 is continued to transmit to the shaft member 12. That is, since the shaft member 12 receives the rotational resistance of the rotor 14 in addition to the sliding resistance of the clutch member 13, the shaft member 12 continues to receive large rotational resistance.

When the shaft member 12 is rotated in the direction of arrow R2 (clockwise) in FIG. 3 from the state where the clutch member 13 and the rotor 14 are linked, the clutch member 13 is displaced upward, and the clutch-side gear 13c and the rotor-side gear 14c are separated from the other. At this time, since the linkage between the clutch member 13 and the rotor 14 is released, the rotational resistance of the rotor 14 is not transmitted to the shaft member 12. That is, the shaft member 12 receives only the sliding resistance of the clutch member 13 as the rotational resistance (the rotational resistance decreases).

Note that the damper 1 is not limited to such a configuration but broadly includes ones that damp the rotation of one member (second object) of two members which is rotatably attached to the other member (first object).

In addition, the damper 1 is not limited to one that damps the rotation in the closing direction of the lid 2b rotatably attached to the body 2a of the box member 2 but can also be configured to damp the rotation in the opening direction of the lid 2b.

The damper 1 includes a sensor 20 and a control unit 21.

The sensor 20 detects a change in a predetermined external environment in the damper 1 or around the damper 1. The sensor 20 is constituted by at least any one of: a rotational speed sensor that detects the rotational speed of the lid 2b with respect to the body 2a (the rotational speed of the rotational part 1B with respect to the casing 1A) (e.g., a magnetic encoder, an optical encoder, a gyro sensor, etc.); a vibration sensor that detects the amount of vibration of the damper 1 (the casing 1A or the rotational part 1B); a load sensor that detects a load applied to a predetermined location of the damper 1 (e.g., the rotor 14 or the clutch member 13 disposed in the tubular member 10); an angle sensor that detects the opening angle of the lid 2b with respect to the body 2a (the opening angle of the rotational part 1B with respect to the casing 1A) (e.g., a magnetic encoder, an optical encoder, a gyro sensor, etc.); a temperature sensor that detects a temperature (the temperature in the damper 1 or the temperature around the damper 1); an atmospheric pressure sensor that detects atmospheric pressure around the damper 1; an odor sensor that detects a predetermined component constituting an odor; a gas sensor that detects a predetermined gas; a dust sensor that detects an amount of dust; and an illumination sensor that detects illumination.

The sensor 20 is disposed in a sensor placement chamber 22. The sensor placement chamber 22 is provided in a predetermined location where the sensor 20 can detect the change in the external environment in the damper 1 (e.g., in the casing 1A). The sensor 20 can also be disposed outside the damper 1 (e.g., outside the casing 1A).

The control unit 21 controls various operations of the damper 1 (sensor 20). The control unit 21 includes a storage device that stores various pieces of information, a clock function (e.g., a real-time clock), a communication circuit 21a that transmits various pieces of information to the outside by wire or wirelessly, an analog-to-digital conversion circuit, a micro-processing unit (MPU), and the like. The control unit 21 stores, into the storage device, information on a rotation state (open/closed state) of the lid 2b of the box member 2, information on the change in the external environment detected by the sensor 20, information on the time when the sensor 20 has detected the change in the external environment, and the like. The control unit 21 transmits the information on the rotating state of the lid 2b of the box member 2, the information on the change in the external environment detected by the sensor 20, the information on the time when the sensor 20 has detected the change in the external environment, and the like from the communication circuit 21a to the outside (e.g., a management server, external communication equipment, a management center, etc.) through a communication network such as the internet. Further, the control unit 21 stores information on the operation mode of the sensor 20 received from the outside, and also receives instruction information received from the outside (information on timing when the sensor 20 detects a change in the external environment information about a predetermined threshold determined by the control unit 21, information about the timing at which the control unit 21 transmits information about a change in the external environment detected by the sensor 20, and the like) is movably constituted based on the instruction information.

Instead of being provided in the damper 1, the control unit 21 can also be constituted by a microcomputer or the like built in the box member 2, or constituted by connection equipment such as a personal computer (PC) electrically connected to the box member 2. The damper 1 can be made compact by disposing the control unit 21 outside the damper 1 as described above.

Further, the control unit 21 can also be configured to transmit the information on the change in the external environment detected by the sensor 20, the information on the time when the sensor 20 has detected a change in the external environment, and the like, from the communication circuit 21*a* to connection equipment (e.g., a beacon device, a wireless module, etc.) disposed inside the damper 1 or outside the damper 1 and connected to the control unit 21, and transmit the information to the outside via the connection equipment.

The sensor 20 constantly performs the operation of detecting the change in the external environment. The meaning of "the sensor 20 constantly performs the operation of detecting the change in the external environment" includes, in addition to a state in which the sensor 20 constantly detects the change in the external environment in a strict sense, a state in which the sensor 20 performs the operation of detecting the change in the external environment at extremely short intervals (e.g., at intervals of less than one second).

Each time the sensor 20 performs the operation of detecting the change in the external environment, the control unit 21 transmits the information on the change in the external environment detected by the sensor 20 and the information on the time when the sensor 20 has detected the change in the external environment to the outside. An external person receives the information on the change in the external environment detected by the sensor 20 and the information on the time when the sensor 20 has detected the change in the external environment via the management server or the like or directly from the damper 1.

In this manner, it is possible to cause an external person at a remote location to constantly grasp the state of the damper 1 or the surrounding conditions of the damper 1 based on the information on the change in the external environment detected by the sensor 20, the information on the time when the sensor 20 has detected the change in the external environment, and the like. Therefore, according to the damper 1, it is possible to more reliably prevent a defect, a failure, and the like from occurring, and it is possible to efficiently conduct repair and inspection work.

The sensor 20 can also be set to perform the operation of detecting the change in the external environment every predetermined time (at least every several seconds (e.g., every 10 minutes or every 180 minutes)). With such a configuration, it is possible to reduce the power consumption generated due to the operation by the sensor 20 to detect the change in the external environment while transmitting the information on the change in the external environment detected by the sensor 20, and the like to the outside, every predetermined time.

Further, the sensor 20 can also be set to perform the operation of detecting the change in the external environment only when the lid 2*b* of the box member 2 is in the open state or in the rotating state. With such a configuration, for example, in a case where various pieces of equipment such as the box member 2 provided with the damper 1 are ones that greatly exhibit a change in the external environment despite there being no defect of the damper 1 when the lid 2*b* is in the closed state, such confusing information at the time of the lid 2*b* being in the closed state can be prevented from being transmitted from the outside.

Further, the sensor 20 can also be set to perform the operation of detecting the change in the external environment only when the lid 2*b* of the box member 2 is in the closed state. With such a configuration, for example, in a case where various pieces of equipment such as the box member 2 provided with the damper 1 are ones that greatly exhibit a change in the external environment despite there being no defect of the damper 1 when the lid 2*b* is in the open state, such confusing information at the time of the lid 2*b* being in the open state can be prevented from being transmitted to the outside.

The control unit 21 can also be set to transmit, to the outside, the information on the change in the external environment detected by the sensor 20 and the information on the time when the sensor 20 has detected the change in the external environment every predetermined time (at least every several seconds (e.g., every 10 minutes, every 180 minutes, or every several days)). With such a configuration, while the information on the change in the external environment detected by the sensor 20, and the like is transmitted to the outside every predetermined time, to cause the external person at the remote location to grasp the state of the damper 1 or the surrounding conditions of the damper 1 every predetermined time, it is possible to reduce power consumption generated due to the operation by the control unit 21 to transmit the information on the change in the external environment, and the like to the outside.

The control unit 21 can also be set to determine whether or not the change in the external environment detected by the sensor 20 is higher than a predetermined threshold. The predetermined threshold is set in advance and stored into the storage device of the control device, and its value can also be changed by external communication or the like.

At this time, it can also be set such that, when the change in the external environment detected by the sensor 20 is higher than the predetermined threshold, the control unit 21 transmits the information on the change in the external environment detected by the sensor 20 in the case of the change being higher than the predetermined threshold and the information on the time when the sensor 20 has detected the change in the external environment to the outside. With such a configuration, when the change in the external environment detected by the sensor 20 exceeds the predetermined threshold (e.g., only when the change in the external environment detected by the sensor 20 has a high degree of abnormality), while the information on the change in the external environment detected by the sensor 20, and the like are transmitted to the outside, to cause the external person at the remote location to grasp the state of the damper 1 or the surrounding conditions of the damper 1 and the state in which the change in the external environment detected by the sensor 20 has exceeded the predetermined threshold, it is possible to reduce power consumption generated due to the operation by the control unit 21 to transmit the information on the change in the external environment, and the like to the outside.

For example, when the damper 1 is provided on a laptop computer or the like and the sensor 20 is constituted by a rotational speed sensor capable of detecting the rotational speed of the rotational part 1B with respect to the casing 1A (e.g., the rotational speed of the screen part with respect to the body of the laptop computer), in a case where the rotational speed of the rotational part 1B with respect to the casing 1A detected by the sensor 20 is higher than a predetermined threshold, the control unit 21 transmits, to the outside, information on the rotational speed of the rotational part 1B with respect to the casing 1A detected by the sensor 20 and information on the time when the sensor 20 has detected the rotational speed of the rotational part 1B with respect to the casing 1A. In this manner, it is possible to cause the external person to grasp that a defect might have occurred in which the rotational speed of the rotational part 1B with respect to the casing 1A has become faster or slower than an initial value that is considered to be in a favorable state due to long-term use or the like. As thus described, it is possible to cause the external person to grasp that there is a possibility that the rotational speed of the rotation part 1B with respect to the case 1A has increased or decreased due to a defect (a defect such as deviation of the casing 1A and the rotational part 1B or deterioration of the damper 1), and it is possible to encourage the maintenance or the like.

Further, for example, when the damper 1 is provided on a laptop computer or the like and the sensor 20 is constituted by a vibration sensor capable of detecting the amount of vibration of the damper 1, in a case where the amount of vibration of the damper 1 detected by the sensor 20 (e.g., the amplitude, the amount of vibration, or the like of the rotational part 1B with respect to the casing 1A) becomes a value higher than a predetermined threshold, the control unit 21 transmits, to the outside, information on the amount of vibration of the damper 1 detected by the sensor 20 and information on the time when the sensor 20 has detected the amount of vibration of the damper 1. In this manner, it is possible to cause the external person to grasp that a defect might have occurred in which the amount of vibration of the damper 1 has become a value higher than an initial value that is considered to be in a favorable state due to long-term use or the like. As thus described, it is possible to cause the external person to grasp that there is a possibility that the amount of vibration of the damper 1 has become a high value due to a defect (a defect such as deviation of the casing 1A and the rotational part 1B or deterioration of the damper 1), and it is possible to encourage the maintenance or the like.

Further, for example, when the damper 1 is provided on a laptop computer or the like and the sensor 20 is constituted by a load sensor that detects a load applied to a predetermined location of the damper 1, in a case where the load detected by the sensor 20 (e.g., a load applied to the shaft member 12, the clutch member 13, or the rotor 14 when the screen part rotates with respect to the body of the laptop computer) becomes a value higher than a predetermined threshold, the control unit 21 transmits, to the outside, information on the load detected by the sensor 20 and information on the time when the sensor 20 has detected the load. In this manner, it is possible to cause the external person to grasp that a defect might have occurred in which the load applied to the predetermined location of the damper 1 has become higher than an initial value that is considered to be in a favorable state due to long-term use or the like. As thus described, it is possible to cause the external person to grasp that there is a possibility that a load applied to a predetermined location of the damper 1 has become high due to a defect (a defect such as deviation of the casing 1A and the rotational part 1B or a state in which the load of the lid 2b applied to the rotational part 1B (shaft member 12) becomes larger than an assumed load caused by deterioration of the damper 1 or the like), and it is possible to encourage the maintenance or the like.

For example, when the damper 1 is provided on a laptop computer or the like and the sensor 20 is constituted by an opening angle sensor capable of detecting the opening angle of the rotational part 1B with respect to the casing 1A (e.g., the opening angle of the screen part with respect to the body of the laptop computer) and when the rotational part 1B is stopped in the state of opening at a preset angle, in a case where the preset angle of the rotational part 1B with respect to the casing 1A detected by the sensor 20 deviates from a predetermined threshold, the control unit 21 transmits, to the outside, information on the opening angle of the rotational part 1B with respect to the casing 1A detected by the sensor 20 and information on the time when the sensor 20 has detected the opening angle of the rotational part 1B with respect to the casing 1A. In this manner, it is possible to cause the external person to grasp that a defect might have occurred in which the opening angle of the rotational part 1B with respect to the casing 1A deviates from an initial value (preset opening angle) that is considered to be in a favorable state due to long-term use or the like As thus described, it is possible to cause the external person to grasp that there is a possibility that the opening angle of the rotation part 1B with respect to the case 1A has deviated from a preset one due to a defect (a defect such as deviation of the casing 1A and the rotational part 1B or deterioration of the damper 1), and it is possible to encourage the maintenance or the like.

For example, when the sensor 20 is constituted by a temperature sensor capable of detecting the temperature of the damper 1, in a case where the temperature of the damper 1 (in the damper 1 or around the damper 1) detected by the sensor 20 is higher or lower than a predetermined threshold, the control unit 21 transmits, to the outside, information on the temperature of the damper 1 detected by the sensor 20 and information on the time when the sensor 20 has detected the temperature of the damper 1. In this manner, it is possible to cause the external person to grasp that a defect might have occurred in which the temperature of the damper 1 has become high or low, such as that abnormal friction has occurred between the members constituting the damper 1 to generate heat or that cool air is leaking from the inside of the freezer or the like, due to long-term use or the like. As thus described, it is possible to cause the external person to grasp that there is a possibility that the temperature of the damper 1 has become high or low due to a defect (a defect such as deviation of the damper 1), and to encourage the maintenance or the like.

For example, when the sensor 20 is constituted by an atmospheric pressure sensor capable of detecting atmospheric pressure around the damper 1, in a case where the atmospheric pressure around the damper 1 detected by the sensor 20 is higher or lower than a predetermined threshold, the control unit 21 transmits, to the outside, information on the atmospheric pressure around the damper 1 detected by the sensor 20 and information on the time when the sensor 20 has detected the atmospheric pressure around the damper 1. In this manner, it is possible to cause the external person to grasp that the damper 1 in a pot or the equipment provided with the damper 1 is being used in an environment with higher atmospheric pressure than in an assumed environment (pressure inside a rice cooker or the like is abnormally high even with the lid 2b in the closed state etc.) or lower atmospheric pressure than in an assumed environment.

Further, for example, when the sensor 20 is constituted by an odor sensor capable of detecting an odor of hydraulic oil filling the space S, in a case where the odor of the hydraulic oil component detected by the sensor 20 is higher than a predetermined threshold, the control unit 21 transmits, to the outside, information on the odor of the hydraulic oil component detected by the sensor 20 and information on the time when the sensor 20 has detected the odor of the hydraulic oil component. In this manner, it is possible to cause the external person to grasp that a defect might have occurred in which the hydraulic oil has leaked. Thereby, for example, the defect of the leakage of the hydraulic oil filling the space S, which has not formed at the time of shipment, can be detected and notified to the outside at an early stage of delivery, or the like, to eliminate at an early stage the deterioration in defect conditions of the damper 1 caused by the hydraulic oil leakage.

Further, for example, when the damper 1 is provided on a wall of a furnace and the sensor 20 is constituted by a gas sensor capable of detecting leakage of a flammable gas out of the furnace through the opening of the furnace, in a case where the combustible gas detected by the sensor 20 is higher than a predetermined threshold, the control unit 21 transmits, to the outside, information on the combustible gas detected by the sensor 20 and information on the time when the sensor 20 has detected the combustible gas. In this manner, it is possible to cause the external person to grasp that there is a possibility that the flammable gas has leaked from the inside of the furnace to the outside of the furnace due to a defect (a defect such as deviation of the damper 1).

Further, for example, when the sensor 20 is constituted by a dust sensor capable of detecting dust inside the damper 1, in a case where the amount of dust inside the damper 1 detected by the sensor 20 is higher than a predetermined threshold, the control unit 21 transmits, to the outside, information on the amount of dust detected by the sensor 20 and information on the time when the sensor 20 has detected the amount of dust. In this manner, it is possible to cause the external person to grasp that there is a possibility that dust has entered the damper 1 due to a defect (a defect such as deviation of the damper 1).

Further, for example, when the sensor 20 is constituted by an illumination sensor capable of detecting illuminance inside the damper 1, in a case where the illumination inside the damper 1 detected by the sensor 20 is higher (brighter) than a treatment threshold, the control unit 21 transmits, to the outside, information on the illuminance inside the damper 1 detected by the sensor 20 and information on the time when the sensor 20 has detected the illuminance inside the damper 1. In this manner, it is possible to cause the external person to grasp that there is a possibility that light has entered the damper 1 due to a defect (a defect such as deviation of the damper 1).

The predetermined threshold can be set in a plurality of stages, and the control unit 21 can also be set to determine whether or not the change in the external environment detected by the sensor 20 is higher than the predetermined threshold in each of the plurality of stages. For example, the predetermined thresholds in the plurality of stages are configured in two stages: a first-stage threshold having a relatively low value and a second-stage threshold having a relatively high value. With such a configuration, it is possible to cause the external person to sequentially grasp a state where the degree of abnormality of the change in the external environment detected by the sensor 20 is relatively low and a state where the degree of abnormality is relatively high.

It is also possible to set such that the predetermined threshold is changed in accordance with the state of the damper 1 (e.g., the open/closed state of the lid 2b of the box member 2, the opening/closing angle of the lid 2b of the box member 2, a time zone, etc.), and the control unit 21 determines whether or not the change in the external environment detected by the sensor 20 is higher than the predetermined threshold having been changed above. For example, the predetermined threshold is set to the relatively low first-stage threshold when the lid 2b is in the closed state, and the predetermined threshold is set to the relatively high second-stage threshold when the lid 2b is in the open state. With such a configuration, for example, the information on the change in the external environment detected by the sensor 20 and the information on the time when the sensor 20 has detected the change in the external environment are transmitted to the outside in a state where the degree of abnormality of the change in the external environment detected by the sensor 20 is relatively low when the lid 2b is in the closed state, and are transmitted to the outside in a state where the degree of abnormality of the change in the external environment detected by the sensor 20 is relatively high when the lid 2b is in the open state.

It is also possible to set such that in a case where the control unit 21 determines whether or not the change in the external environment detected by the sensor 20 is higher than the predetermined threshold, when the control unit 21 determines that "the change in the external environment detected by the sensor 20 is higher than a predetermined threshold" a plurality of times within a predetermined time (e.g., three times within 10 minutes), the control unit 21 transmits the information on the change in the external environment detected by the sensor 20 when the change is higher than the predetermined threshold and the information on the time when the sensor 20 has detected the change in the external environment to the outside. With such a configuration, when the degree of abnormality of the change in the external environment detected by the sensor 20 is not actually high, it is possible to prevent the control unit 21 from determining that the change in the external environment detected by the sensor 20 based on noise or the like is higher than the predetermined threshold and from transmitting the information to the outside.

It is also possible to set such that in a case where the control unit 21 determines whether or not the change in the external environment detected by the sensor 20 is higher than the predetermined threshold, the control unit 21 performs the operation of determining whether or not the change in the external environment detected by the sensor 20 is higher than the predetermined threshold only when the lid 2b of the box member 2 is in the closed state. With such a configuration, for example, in a case where various pieces of equipment such as the box member 2 provided with the damper 1 are ones that greatly exhibit a change in the external environment despite there being no defect when the lid 2b is in the open state, such confusing information at the time of the lid 2b being in the open state can be prevented from being transmitted to the outside.

It is also possible to set such that in a case where the control unit 21 determines whether or not the change in the external environment detected by the sensor 20 is higher than the predetermined threshold, the control unit 21 performs the operation of determining whether or not the change in the external environment detected by the sensor 20 is higher than the predetermined threshold only when the lid 2b of the box member 2 is in the open state (when the lid 2b is opened at a predetermined opening/closing angle). With such a configuration, for example, in a case where various pieces of equipment such as the box member 2 provided with the damper 1 are ones that greatly exhibit a change in the external environment despite there being no defect when the lid 2b is in the closed state, such confusing information at the time of the lid 2b being in the closed state can be prevented from being transmitted to the outside.

The sensor placement chamber 22 can also be configured to come into a sealed state when the lid 2b is in the closed state. That is, since the sensor placement chamber 22 comes into the sealed state when the lid 2b is in the closed state, the sensor 20 cannot detect the change in the external environment outside the sensor placement chamber 22. Further, the sealed state of the sensor placement chamber 22 is released when the lid 2b is in the open state, and the sensor 20 can detect the change in the external environment outside the sensor placement chamber 22.

With such a configuration, for example, in a case where various pieces of equipment such as the box member 2 provided with the damper 1 have a relatively low concentration of a gas to be detected while the lid 2b is closed, and have a relatively high concentration of the gas to be detected while the lid 2b is open, when the lid 2b is in the open state, the sealed state of the sensor placement chamber 22 can be released to bring the sensor 20 into the state of being able to detect the gas to be detected, and when the lid 2b is in the closed state, the sensor 20 can be prevented from deteriorating at an early stage by being exposed to a high-concentration gas to be detected, or the like.

The sensor placement chamber 22 can also be configured to be in the sealed state when the lid 2b is in the open state (or when the lid 2b is in the maximum open state (e.g., the rotation angle θ=180 degrees)). That is, since the sensor placement chamber 22 comes into the sealed state when the lid 2b is in the open state, the sensor 20 cannot detect the change in the external environment outside the sensor placement chamber 22. Further, the sealed state of the sensor placement chamber 22 is released when the lid 2b is in the closed state, and the sensor 20 can detect the change in the external environment outside the sensor placement chamber 22.

With such a configuration, for example, in a case where various pieces of equipment such as the box member 2 provided with the damper 1 have a relatively low concentration of a gas to be detected while the lid 2b is open, and have a relatively high concentration of the gas to be detected while the lid 2b is closed, when the lid 2b is in the open state, the sealed state of the sensor placement chamber 22 can be released to bring the sensor 20 into the state of being able to detect the gas to be detected, and when the lid 2b is in the open state, the sensor 20 can be prevented from deteriorating at an early stage by being exposed to a high-concentration gas to be detected, or the like.

INDUSTRIAL APPLICABILITY

The present invention is used for a damper that damps rotation of a second object rotatably attached to a first object in either a closing direction or an opening direction, and a damper monitoring method.

REFERENCE SIGNS LIST

1 Damper
1A Casing
1B Rotational part
2 Box member
2a Body
2b Lid
10 Tubular member
11 Lid member
12 Shaft member
13 Clutch member
14 Rotor
20 Sensor
21 Control unit
22 Sensor placement chamber

The invention claimed is:
1. A damper comprising:
a casing linked to a first object; and
a rotational part linked to a second object rotatably attached to the first object, the damper damping rotation of the second object in either a closing direction or an opening direction,
the damper including:
a sensor that detects a predetermined change in an external environment in the damper or around the damper; and
a control unit that transmits information on the change in the external environment, detected by the sensor, to the outside through a communication network, in which
the sensor is constituted by at least any one of a rotational speed sensor that detects a rotational speed of the rotational part with respect to the casing, a vibration sensor that detects an amount of vibration, a load sensor that detects a load, an angle sensor that detects an opening angle of the rotational part with respect to the casing, a temperature sensor that detects a temperature, an atmospheric pressure sensor that detects atmospheric pressure, an odor sensor that detects a predetermined component constituting an odor, a gas sensor that detects a predetermined gas, a dust sensor that detects an amount of dust, and an illumination sensor that detects illumination, the control unit determines whether or not the external environment change detected by the sensor is higher than the predetermined threshold, when the external environment change detected by the sensor is higher than the predetermined threshold, the control unit transmits the information on the change in the external environment detected by the sensor to the outside,
the predetermined threshold is set in a plurality of stages having different values from each other, and
the control unit is set to determine whether or not the external environment change is higher than the predetermined threshold in each of the plurality of stages.
2. A monitoring method for a damper includes:
a casing linked to a first object; and
a rotational part linked to a second object,
the damper being rotatably linking the second object to the first object,
a sensor provided in the damper detecting a predetermined change in an external environment in the damper or around the damper; and
a control unit transmitting information on the change in the external environment, detected by the sensor, to the outside through a communication network, in which
the sensor is constituted by at least any one of
a rotation count sensor that detects the number of times of rotation of the rotational part with respect to the casing,
a sound sensor that detects a sound of the rotational part during a rotating operation with respect to the casing,
a temperature sensor that detects a temperature, and
a torque sensor that detects torque based on a frictional force of the rotational part during rotation with respect to the casing,
the control unit determines whether or not the external environment change detected by the sensor is higher than the predetermined threshold, when the external environment change detected by the sensor is higher than the predetermined threshold, the control unit transmits the information on the change in the external environment detected by the sensor to the outside,
the predetermined threshold is set in a plurality of stages having different values from each other, and
the control unit is set to determine whether or not the external environment change is higher than the predetermined threshold in each of the plurality of stages.

* * * * *